United States Patent
Brewer et al.

(10) Patent No.: US 9,750,533 B2
(45) Date of Patent: Sep. 5, 2017

(54) EXFOLIATING HEAD FOR A PERSONAL CARE APPLIANCE

(71) Applicant: L'Oreal, Paris (FR)

(72) Inventors: Gerald Keith Brewer, Redmond, WA (US); Ricky Wai Kit Chan, Bellevue, WA (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/862,264

(22) Filed: Apr. 12, 2013

(65) Prior Publication Data
US 2014/0305458 A1    Oct. 16, 2014

(51) Int. Cl.
*A61B 17/50* (2006.01)
*A61B 17/54* (2006.01)
*A45D 34/04* (2006.01)
*A61B 17/00* (2006.01)
*A61B 17/32* (2006.01)

(52) U.S. Cl.
CPC ............ *A61B 17/54* (2013.01); *A45D 34/041* (2013.01); *A45D 2200/1054* (2013.01); *A45D 2200/207* (2013.01); *A61B 2017/00398* (2013.01); *A61B 2017/00734* (2013.01); *A61B 2017/320004* (2013.01)

(58) Field of Classification Search
CPC ....................... A61B 17/50; A61B 5/06; A61B 2017/00761; A61B 17/322; A61B 606/131
USPC ..................... 606/131; 601/114, 142; 15/28; 451/358, 359, 356, 357, 344
See application file for complete search history.

(56) References Cited

U.S. PATENT DOCUMENTS 1,953,983 A  *  4/1934  Benner ................... B24D 11/00
                                                             451/359
2,099,179 A  *  11/1937  Stainbrook ........... B24B 19/165
                                                             451/285
(Continued)

FOREIGN PATENT DOCUMENTS

CN            1972612 A        5/2007
DE    20 2007 003 972 U1      7/2007
(Continued)

OTHER PUBLICATIONS

Invitation to Pay Additional Fees and Communication Relating to the Results of the Partial International Search mailed Jul. 4, 2014, issued in corresponding International Application No. PCT/2014/33845, filed Apr. 11, 2014, 6 pages.
(Continued)

*Primary Examiner* — Amy R Weisberg
(74) *Attorney, Agent, or Firm* — Christensen O'Connor Johnson Kindness PLLC (57) ABSTRACT

Exfoliating heads with an abrasive surface are disclosed for use with a personal care appliance. The personal care appliance is configured to oscillate the exfoliating head to provide improved smoothing and exfoliation of a subject's epidermis with or without the antecedent application of skin care formula. The oscillating action of the exfoliating head may be rotational, translational, or a combination thereof. In use, the personal care appliance oscillates the abrasive surface of the exfoliating head over a subject's skin in order to remove dead skin from the subject's epidermis. The exfoliating heads may be used to treat rough skin conditions, such as calluses or corns, which have developed on a patient's hand or foot.

20 Claims, 7 Drawing Sheets

(56) References Cited

U.S. PATENT DOCUMENTS

| | | | | |
|---|---|---|---|---|
| 2,714,788 | A * | 8/1955 | Di Giovanna | A45D 26/0004 132/73.6 |
| 2,922,261 | A * | 1/1960 | Rabkin | B24B 23/02 132/73.6 |
| 6,123,612 | A * | 9/2000 | Goers | B24B 53/017 451/540 |
| 6,283,845 | B1 * | 9/2001 | Fischbacher | B24B 55/02 451/542 |
| 6,371,842 | B1 * | 4/2002 | Romero | B24D 11/001 451/540 |
| 6,629,983 | B1 * | 10/2003 | Ignon | A61B 17/54 606/131 |
| 6,821,196 | B2 * | 11/2004 | Oliver | B24D 18/0009 451/544 |
| 7,044,938 | B2 * | 5/2006 | La Bianco | A61B 17/54 401/133 |
| D524,441 | S | 7/2006 | Anderson | |
| 7,150,677 | B2 * | 12/2006 | Yamashita | B24B 53/12 451/443 |
| 7,270,641 | B2 * | 9/2007 | Glucksman | A45D 26/0004 601/112 |
| 7,384,377 | B2 * | 6/2008 | Berman | A61H 7/005 482/11 |
| 7,386,906 | B2 * | 6/2008 | Roth et al. | 15/28 |
| 7,581,545 | B1 * | 9/2009 | Moldawski | A45D 40/22 132/73.6 |
| 7,786,626 | B2 | 8/2010 | Reishus | |
| D623,801 | S | 9/2010 | Curran | |
| 7,846,488 | B2 * | 12/2010 | Johnson | A61K 9/0021 324/754.03 |
| 8,048,089 | B2 * | 11/2011 | Ignon | A61B 17/545 606/1 |
| 8,066,013 | B2 * | 11/2011 | Tes | A61B 17/54 132/73.6 |
| 8,236,008 | B2 * | 8/2012 | Boone, III | A61B 17/545 451/344 |
| 8,292,696 | B2 * | 10/2012 | Sugimura | A61M 37/0015 451/28 |
| 8,343,116 | B2 * | 1/2013 | Ignon | A61M 35/003 604/289 |
| 8,425,278 | B2 * | 4/2013 | Culler | B24D 11/00 451/41 |
| 8,900,180 | B2 * | 12/2014 | Wolter | A61K 9/0021 604/46 |
| 8,900,194 | B2 * | 12/2014 | Clarke | A61K 9/0021 604/173 |
| 9,114,238 | B2 * | 8/2015 | Singh | A61K 9/0021 |
| 9,314,903 | B2 * | 4/2016 | Woo | B24D 3/28 |
| 2002/0107527 | A1 * | 8/2002 | Burres | A45D 29/14 606/131 |
| 2002/0177858 | A1 * | 11/2002 | Sherman | A45D 26/0004 606/131 |
| 2003/0125754 | A1 * | 7/2003 | Davis | A45D 26/0004 606/133 |
| 2003/0199811 | A1 * | 10/2003 | Sage, Jr. | A61B 17/205 604/46 |
| 2003/0220656 | A1 * | 11/2003 | Gartstein | A45D 26/0004 606/131 |
| 2004/0005851 | A1 * | 1/2004 | MacKay | B24D 13/20 451/359 |
| 2004/0162565 | A1 * | 8/2004 | Carson | A61B 10/02 606/131 |
| 2005/0199265 | A1 * | 9/2005 | France et al. | 134/6 |
| 2005/0203575 | A1 * | 9/2005 | Carson | A61M 37/0015 606/204.35 |
| 2006/0009719 | A1 * | 1/2006 | LaJoie | A45D 33/005 601/70 |
| 2006/0116694 | A1 * | 6/2006 | Hogan | A45D 34/04 606/131 |
| 2006/0137703 | A1 | 6/2006 | Kling | |
| 2006/0178676 | A1 | 8/2006 | Anderson | |
| 2006/0211961 | A1 * | 9/2006 | Meyer | A61H 7/005 601/73 |
| 2007/0005078 | A1 * | 1/2007 | Hart | A61B 17/54 606/131 |
| 2007/0049176 | A1 * | 3/2007 | Jones | B24B 23/028 451/28 |
| 2007/0099552 | A1 * | 5/2007 | Chen | B24B 37/046 451/548 |
| 2007/0155293 | A1 * | 7/2007 | Endres | C03C 10/00 451/56 |
| 2007/0221238 | A1 * | 9/2007 | Tran | 132/73.6 |
| 2009/0083916 | A1 * | 4/2009 | Lampka | B24B 23/028 15/3.53 |
| 2009/0104862 | A1 * | 4/2009 | MacKay | B24B 45/006 451/359 |
| 2009/0221212 | A1 * | 9/2009 | Palushaj | A46B 13/008 451/28 |
| 2009/0222024 | A1 * | 9/2009 | Naldoni | A61B 17/54 606/131 |
| 2010/0049177 | A1 * | 2/2010 | Boone, III | A61H 9/0057 606/9 |
| 2010/0198169 | A1 * | 8/2010 | Sugimura | A61M 37/0015 604/272 |
| 2010/0217263 | A1 * | 8/2010 | Tukulj-Popovic | A45D 26/0004 606/43 |
| 2010/0323593 | A1 * | 12/2010 | Hoeschele | B25F 5/008 451/359 |
| 2012/0016379 | A1 * | 1/2012 | Kay | A61B 17/54 606/131 |
| 2012/0330250 | A1 * | 12/2012 | Kuwahara | A61M 37/0015 604/272 |
| 2013/0023901 | A1 * | 1/2013 | Sanchez-Martinez | A46B 13/008 606/133 |
| 2013/0090043 | A1 * | 4/2013 | Mueller | B23F 23/1225 451/47 |
| 2013/0138119 | A1 * | 5/2013 | Luzon | A61B 17/54 606/131 |
| 2013/0158547 | A1 * | 6/2013 | David | A61B 18/14 606/41 |
| 2013/0274762 | A1 * | 10/2013 | Guay | A45D 44/22 606/131 |
| 2013/0345721 | A1 * | 12/2013 | Menke | A61B 17/54 606/131 |
| 2014/0135798 | A1 * | 5/2014 | David | A61B 17/54 606/131 |
| 2014/0305458 | A1 * | 10/2014 | Brewer | A45D 34/041 132/200 |
| 2014/0330289 | A1 * | 11/2014 | Revivo | A61B 17/54 606/131 |
| 2015/0245853 | A1 * | 9/2015 | Jakubow | A61B 17/54 606/131 |
| 2015/0272623 | A1 * | 10/2015 | Ignon | A61B 17/545 606/131 |
| 2016/0052102 | A1 * | 2/2016 | Sato | B24B 23/005 451/359 |
| 2016/0193717 | A1 * | 7/2016 | Culler | B24D 3/20 451/540 |

FOREIGN PATENT DOCUMENTS

| | | |
|---|---|---|
| EP | 2082696 B1 | 7/2009 |
| WO | 01/56529 A2 | 8/2001 |
| WO | 2005/091748 A2 | 10/2005 |
| WO | 2007/080596 A2 | 7/2007 |
| WO | 2008/098648 A1 | 8/2008 |
| WO | 2009/038305 A2 | 3/2009 |
| WO | 2009/148729 A2 | 12/2009 |

OTHER PUBLICATIONS

International Search Report mailed Oct. 1, 2014, issued in corresponding International Application No. PCT/US2014/033845, filed Apr. 11, 2014, 6 pages.

Written Opinion of the International Searching Authority mailed Oct. 1, 2014, issued in corresponding International Application No. PCT/US2014/033845, filed Apr. 11, 2014, 13 pages.
Chinese Office Action mailed Sep. 21, 2016, issued in corresponding Application No. CN 201480030246.1, filed Apr. 10, 2014, 19 pages.

* cited by examiner

EXFOLIATING HEAD FOR A PERSONAL CARE APPLIANCE

BACKGROUND

As is well known to those skilled in the art, thick calluses or corns are typically formed on the palms of the hands or the soles of the feet when the epidermis of the palms or the soles becomes partially keratinized due to frequently repeated contact of the hands or feet with a variety of hard or coarse surfaces over time. For example, calluses on the hands are often caused by the regular handling of an object that puts pressure on the hand, such as tools or sports equipment. Calluses and corns on the feet are often caused by pressure from footwear such as tight shoes, high-heeled shoes, loose shoes, and thin-sole shoes. The repeated pressure due to contact causes the skin to die and form a hard, protective surface.

Calluses and corns can cause discomfort and can also become painful. Moreover, calluses or corns crack due to, for example, dry or cold weather, thus allowing the dermis under the epidermis to be damaged. Therefore, it is often necessary to periodically remove such calluses or corns from the palms of the hands or soles of the feet. Such removal of calluses or corns from the hands or feet is commonly called "a pedicure."

During a pedicure, calluses and dry, flaky skin are abraded or scraped from the bottom of the feet. Typically, the feet are soaked in a warm bath and/or a topical formula is applied to soften the skin. Once the warm water and/or a topical formula has softened the skin on the feet, the bottoms of the feet are manually scrubbed with either a pedicure sander comprised of an abrasive sanding pad attached to a durable plastic handle, a callus rasp, or a pumice stone. Additionally, some technicians will use a corn and callus plane comprised of a stainless steel head with a raised shaving blade to slice thick, tough callus from the feet.

These conventional methods and apparatuses for callus removal are time consuming, laborious, inefficient, and often painful. Additionally, some of the conventional instruments present hazards. In particular, a callus plane may cause serious injury if used improperly. Accordingly, to reduce the risks and deleterious effects of the manual process, attempts have been made to automate the process of removing skin imperfections from the feet and hands. For example, several electrically powered rotary devices with sandpaper-like contact surfaces have been devised for grooming hands and feet, one such device being sold under the brand name "Pedi-Smooth."

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with aspects of the present application, an exfoliating head is provided for use with a personal care appliance having a drive system. The exfoliating head includes a movable base portion configured to be operatively coupled to the drive system, and a disc plate mounted on the moving base portion. The disc plate in some embodiments includes an outwardly facing contact surface having an abrasive disposed thereon. In some embodiments, the abrasive is configured to exfoliate a partially keratinized area of an epidermis when placed in contact therewith.

In accordance with another aspect of the present disclosure, an exfoliating system is provided. The system includes an appliance having a drive motor configured to oscillate a drive shaft, and a brush-less exfoliating head selectively attached to the appliance. The brush-less exfoliating head includes a movable portion operatively coupled to the drive shaft for oscillating with the drive shaft in response to the drive motor. In some embodiments, the movable portion includes an outwardly facing, generally planar contact surface having a plurality of abrasive elements thereon. Each abrasive element is configured to exfoliate an epidermis when placed in contact therewith.

In accordance with yet another aspect of the present application, a method is provided for exfoliating skin from a subject's epidermis. The method includes oscillating, via a motorized drive system, an exfoliating head having an outer surface with abrasive elements thereon. In some embodiments, the abrasive elements are configured to exfoliate partially keratinized areas of the subject's epidermis. The method also includes applying the abrasive elements against a portion of the subject's epidermis.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The detailed description set forth below in connection with the appended drawings where like numerals reference like elements is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

The following discussion provides examples of systems, apparatuses, and/or methods for exfoliating skin. The examples described herein provide exfoliating heads suitable for use with a personal care appliance. In some examples described herein, the personal care appliance oscillates the exfoliating head to provide improved smoothing and exfoliation of a subject's epidermis with or without the antecedent application of skin care formula. The oscillating action of the exfoliating head may be rotational, translational, or a combination thereof. In use, the personal care appliance oscillates the exfoliating head over a subject's skin in order to remove dead skin from the subject's epidermis. In some embodiments, the exfoliating head is used to treat rough skin conditions, such as calluses or corns, which have developed on a patient's hand or foot. For example, the exfoliating head enables the user to sculpt a rough skin condition into a smooth, polished epidermal surface.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Figure 1:
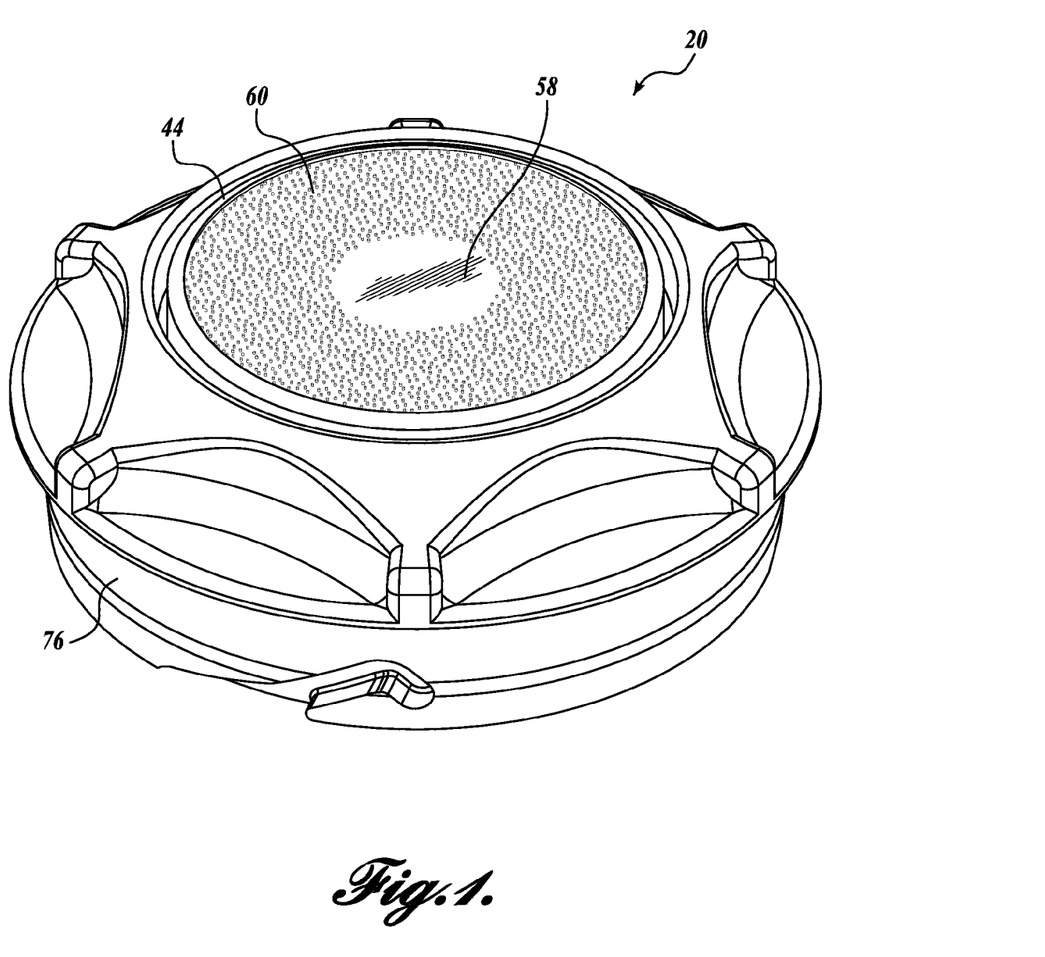
FIG. 1 is a perspective view of one example of an exfoliating head in accordance with aspects of the present disclosure.

Turning now to FIG. 1, there is shown one example of an exfoliating head, generally designated 20, formed in accordance with aspects of the present disclosure. The head 20 is suitable for use with a personal care appliance, such as appliance 22, illustrated in FIGS. 8 and 9. As will be described in more detail below, the head 20 includes a surface 58 with abrasive sections 60 that can be oscillated over a subject's skin in order to remove dead skin cells from the epidermis. As will be also described in more detail below, some embodiments utilize sonic motion for oscillating the head 20, which can provide improved control and precision for sculpting and callus removal.

Prior to describing the head 20 in more detail, one example of a personal care appliance 22 that may be employed to impart an oscillating motion to the head 20 will be described in some detail. While the personal care appliance 22 is one type of appliance that can be practiced with embodiments of the present disclosure, it will be appreciated that the head 20 is suitable for use with a wide range of oscillatory or vibratory motion generating devices.

Figure 8:
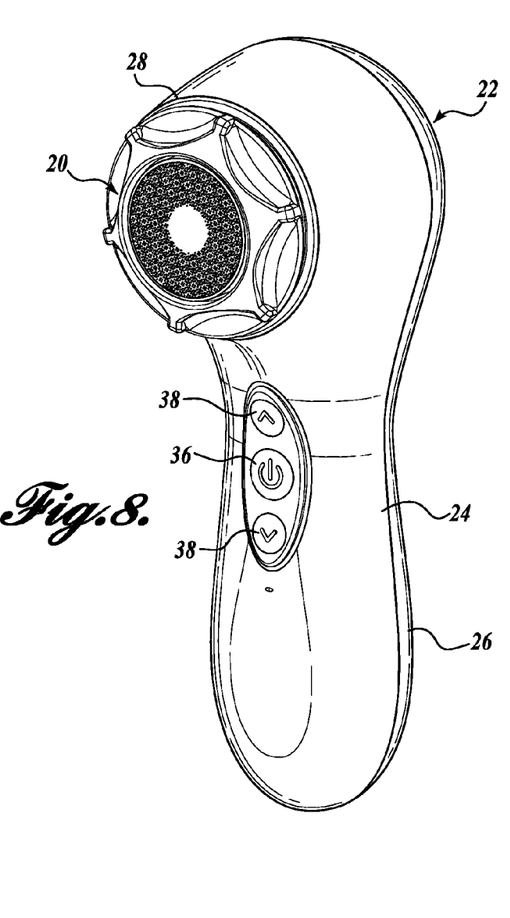
FIG. 8 is a perspective view of one example of a personal care appliance on which an exfoliating head of FIG. 1 is mounted.
Figure 9:
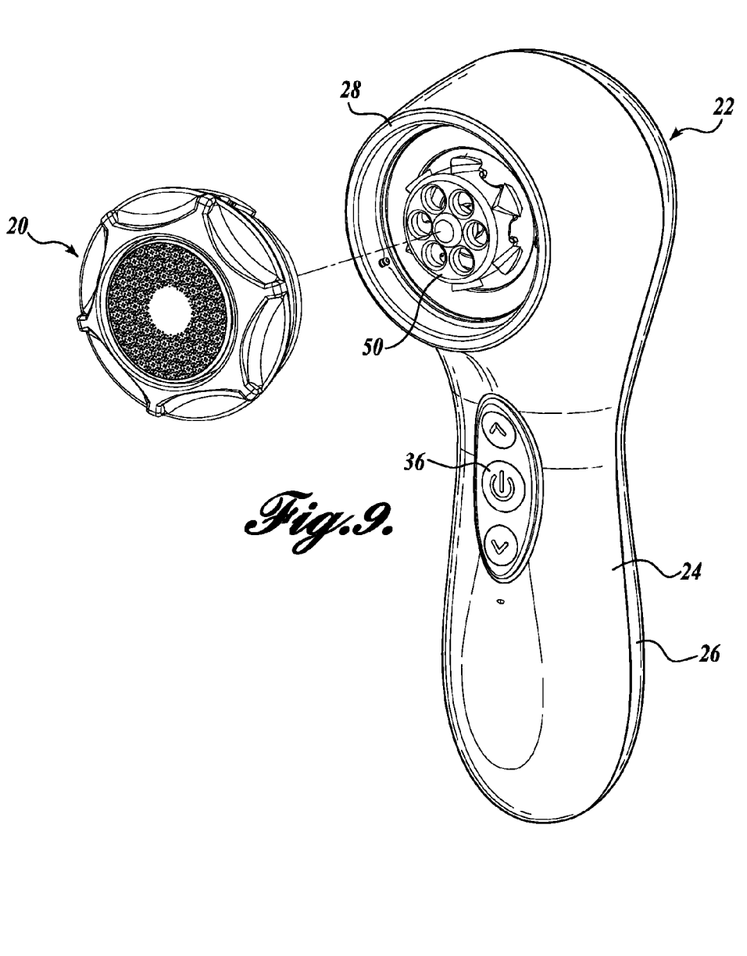
FIG. 9 is a side view of a personal care appliance of FIG. 8 with the exfoliating head exploded therefrom.
Figure 10:
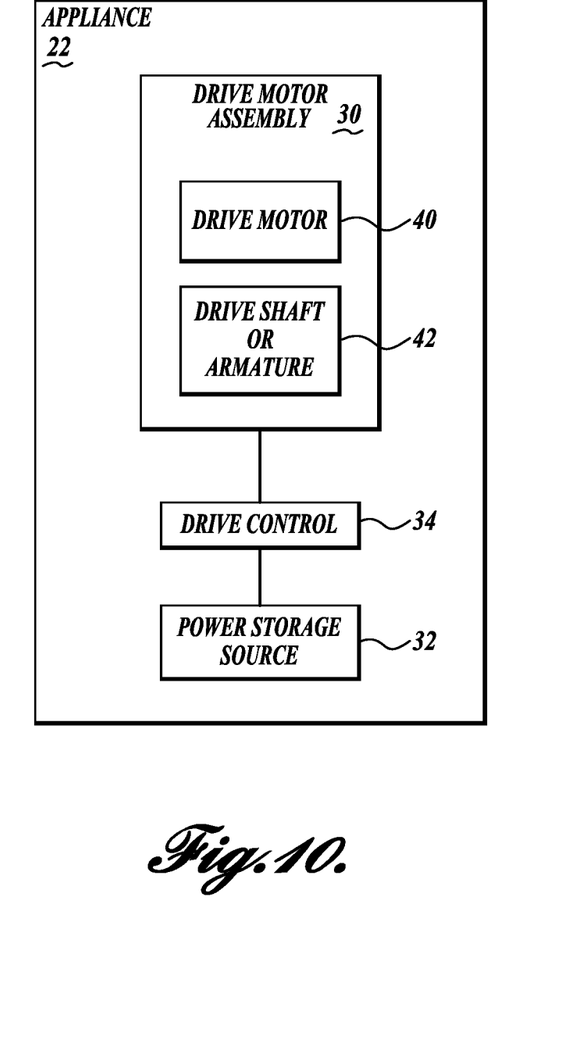
FIG. 10 is a functional block diagram of several components of the personal care appliance of FIG. 8.

Turning now to FIGS. 8 and 9, there is shown one example of the personal care appliance 22. The appliance 22 includes a body 24 having a handle portion 26 and a head attachment portion 28. The head attachment portion 28 is configured to selective attach a head, such as exfoliating head 20, to the appliance 22. The appliance body 24 houses the operating structure of the appliance. As shown in block diagrammatic form in FIG. 10, the operating structure in one embodiment includes a drive motor assembly 30, a power storage source 32, such as a rechargeable battery, and a drive control 34 that includes an on/off button 36 (See FIG. 8) configured and arranged to selectively deliver power from the power storage source 32 to the drive motor assembly 30. In some embodiments, the drive control 34 may also include a power adjust or mode control buttons 38 (See FIG. 8) coupled to control circuitry, such as a programmed microcontroller or processor, which is configured to control the delivery of power to the drive motor assembly 30. The drive motor assembly 30 in some embodiments includes an electric drive motor 40 that drives an attached head, such as exfoliating head 20, via a drive shaft or armature 42.

When a personal care head, such as exfoliating head 20, is mounted to the head attachment portion 28, the drive motor assembly 30 is configured to impart motion to the head 20. The drive motor assembly 30 may be configured to operate the exfoliating head 20 at sonic frequencies, typically in the range of 90-300 Hz, oscillating the exfoliating head 20 back and forth within an angular range of 8-26 degrees. In some embodiments, as will be described in more detail below, the exfoliating head 20 is operated at frequencies between about 100 Hz to 190 Hz with an amplitude or range of about 12-18 degrees. In other embodiments, the exfoliating head 20 is operated at frequencies of about 168 Hz to 178 Hz, amplitudes of about 12-18 degrees, and a duty cycle of about 36-48%.

One example of a drive motor assembly 30 that may be employed by the appliance 22 to oscillate the exfoliating head 20 is shown and described in U.S. Pat. No. 7,786,626, the disclosure of which is hereby incorporated by reference in its entirety. However, it should be understood that this is merely an example of the structure and operation of one such appliance and that the structure, operation frequency and oscillation amplitude of such an appliance could be varied, depending in part on its intended application and/or characteristics of the exfoliating head, such as its inertial properties, etc. In some embodiments of the present disclosure, the frequency ranges are selected so as to drive the attached head at near resonance. Thus, selected frequency ranges are dependent, in part, on the inertial properties of the attached head. It will be appreciated that driving the attached head at near resonance provides many benefits, including the ability to drive the attached head at suitable amplitudes in loaded conditions (e.g. when contacting the skin). For a more detailed discussion on the design parameters of the appliance, please see U.S. Pat. No. 7,786,626.

Figure 2:
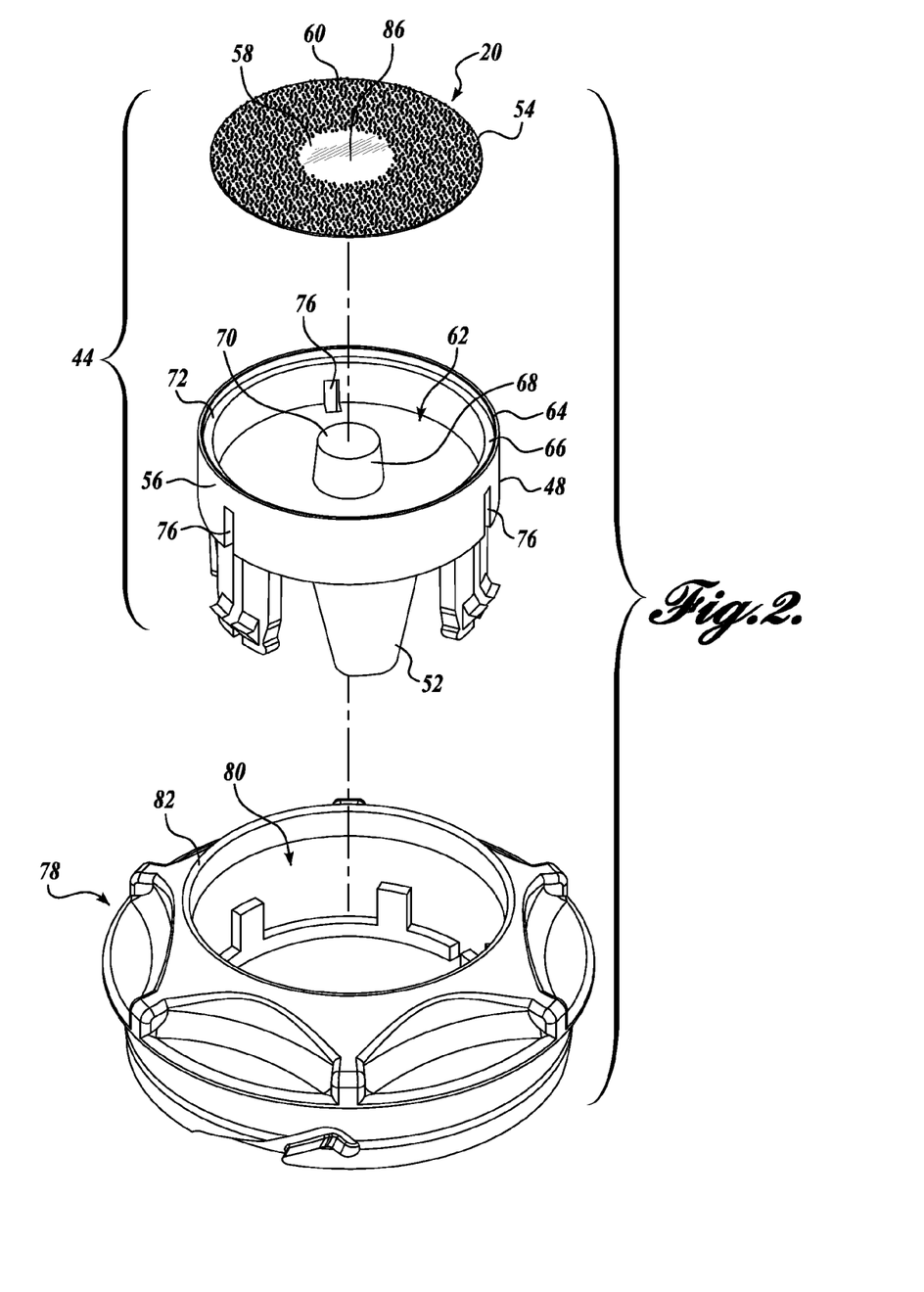
FIG. 2 is an exploded view of the exfoliating head of FIG. 1.
Figure 3:
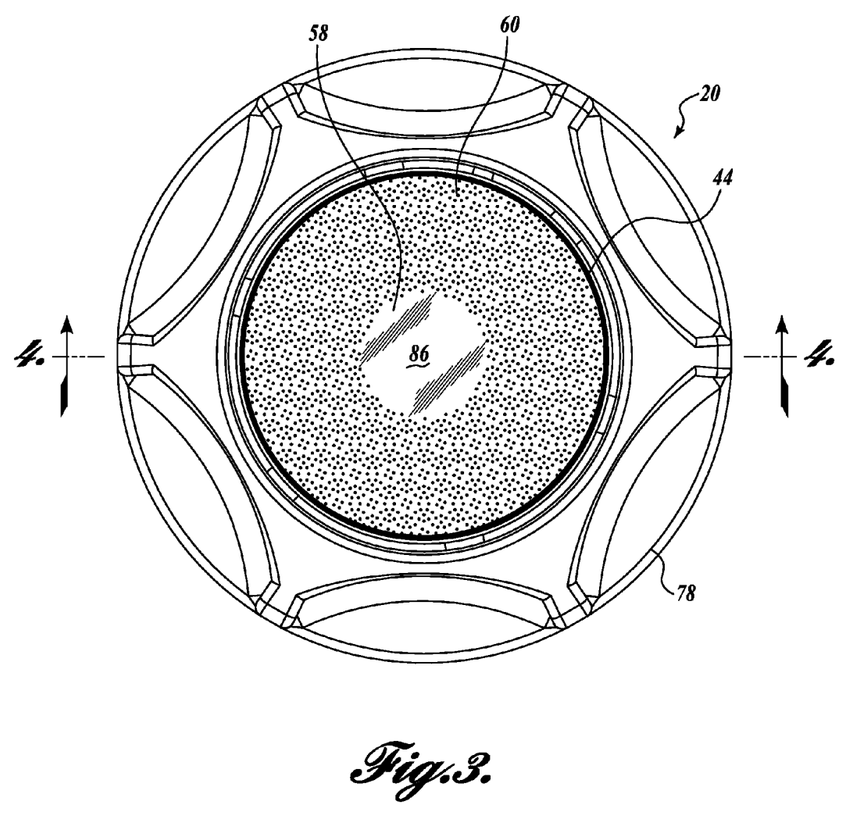
FIG. 3 is a top view of an exfoliating head, such as the exfoliating head of FIG. 1.
Figure 4:
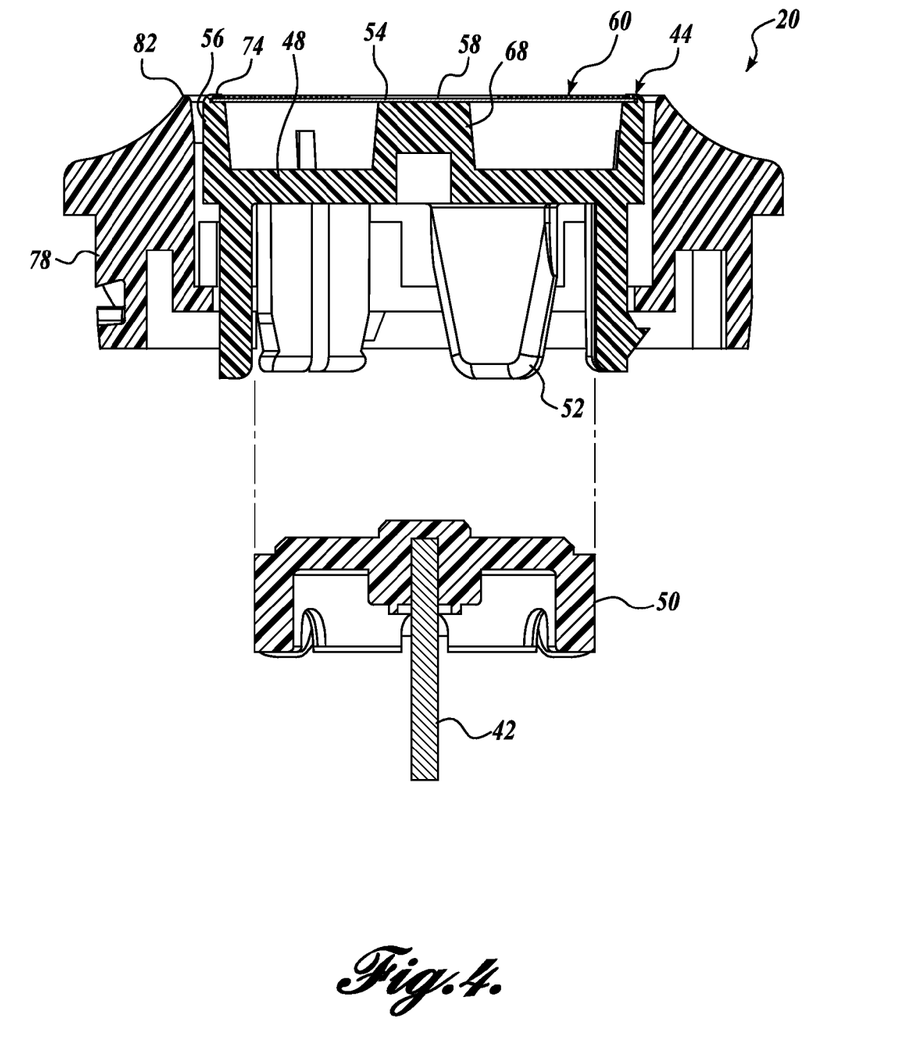
FIG. 4 is a cross-sectional view of the exfoliating head of FIG. 1 adapted to be coupled to components of a drive motor system.

Turning now to FIGS. 2-4, one example of the exfoliating head 20 will be described in more detail. As best shown in FIGS. 2 and 4, the head 20 includes a generally cylindrical, movable central portion 44. The movable central portion 44 includes a base section 48 configured to interface directly or indirectly (e.g., via drive boss 50) with the drive shaft or armature 42 of the drive motor assembly 30 at a first or inner end 52. The base section 48 is shown in FIG. 4 as being constructed out of plastic, such as nylon, polyurethane, polypropylene, polyethylene, etc., although other materials may be utilized, including lightweight metals, such as aluminum, titanium, etc.

The movable central portion 44 further includes a disc plate 54 fixedly attached to the base section 48 at an opposite, second or outer end 56. In the embodiment shown, the disc plate 54 forms the outwardly facing surface 58 of the head 20 having one or more abrasive sections 60. The disc plate 54 is shown in FIG. 3 as being constructed out of metal, such as stainless steel, silver, zinc, brass, copper, aluminum, gold, etc., their alloys, and combinations thereof, although other materials may be utilized, including plastics such as nylon, polyurethane, polypropylene, polyethylene, etc. In some embodiments, the disc plate 54 may include an inner core constructed from a more economical or lighter metal, such as aluminum or stainless steel, and an outer layer constructed from a more biocompatible metal, such as zinc, copper, gold or silver.

In the embodiment shown in FIGS. 2 and 4, the base section 48 includes an open ended cavity 62 defined by a peripherally extending outer rim 64 in conjunction with shoulder or step section 66. Disposed in the center of the cavity 62 is a central boss 68 having a top support surface 70 that is generally co-planar with the support surface 72 of step section 66. To fixedly secure the disc plate 54 to the base section 48 in one embodiment, the disc plate 54 is first placed on and supported by the boss 70 and shoulder 66. The rim 64 is then die formed in order to trap the disc plate 54 between the shoulder 66 and a die-formed flange 74. In some embodiments, the die-formed flange 74 extends over and into engagement with a portion of the abrasive sections 60. It will be appreciated that other securement methods can be employed. For example, the disc plate 54 can be adhesive bonded to the base section 48.

While examples of the movable central portion 44 were shown and described as being a separate base section 48 and disc plate 54, other configurations of the central portion 44 are contemplated by the present disclosure. For example, in some embodiments, the central portion 44 can be a unitary member of metal or plastic, and can be formed by casting, molding, co-molding, or other conventional techniques.

In some embodiments, the base section 48 may also include one or more additional features. For example, the exfoliating head 20 can be specifically engineered for use in a resonant system. In this regard, it may be important to try to maintain the inertial properties of head 20 during operation. Accordingly, one or more drain holes or slots 76 may be provided around the perimeter of inner cavity 72 in order to remove any fluid and/or solids that may access the inner cavity 72. It will be appreciated that when the head 20 is design for use with sonic motion generators, the system (e.g., drive motor assembly 30 and head 20) can be designed to stall if excessive or harmful exfoliating pressure is applied.

Returning to FIG. 2-4, the head 20 further includes an optional outer retainer 78. The outer retainer 78 includes a central, cylindrically shaped opening 80. The opening 80 is sized and configured to surround the sides of the movable central portion 44. When attached to the appliance 22, a rim 82, which extends around the top periphery of the central opening 80, is flush with or positioned slightly below or inwardly (i.e., toward the head attachment portion 28) of the outer surface 58 of the movable central portion 44.

In some embodiments, the central portion 44 and the outer retainer 78 together include an attachment system configured to provide selective attachment of the head 20 to the head attachment portion 28 of the personal care appliance 22. When attached to the personal care appliance 22 by the attachment system, the following occurs: (1) the movable central portion 44 is operatively connected to the drive motor assembly 30, for example, via a drive boss 50, in a manner that provides oscillating motion thereto; and (2) the outer retainer 78 fixedly secures the head 20 to the appliance 22. Accordingly, the attachment system in some embodiments provides a quick and easy technique for attaching and detaching the head 20 to the personal care appliance 22. It will be appreciated that the attachment system also allows for other personal care heads to be attached to the handle, and allows for replacement exfoliating heads to be attached to the appliance 22, when desired.

One attachment system that may be practiced with embodiments of the present disclosure is set forth in U.S. Pat. No. 7,386,906, the disclosure of which is hereby incorporated by reference in its entirety. It will be appreciated that other attachment systems can be employed to provide either tooled or tool-less techniques for selectively attaching the head 20 to a personal care appliance, such as appliance 22, in a manner that (1) provides oscillating motion to the central portion 44; and (2) maintains the connection between the central portion 44 and the drive motor assembly 30. For example, in some embodiments, the central portion 44 includes a coupling interface configured to cooperatingly connect to an oscillating drive shaft or armature, such as armature 42, of an associated drive motor assembly 30 in a manner that transmits oscillating motion to the central portion 44 while fixedly securing the central portion 44 thereto. As such, it should be understood that while the retainer 78 may provide certain benefits to some embodiments of the head 20, it is optional, and thus, it may be omitted, if desired.

Figure 5:
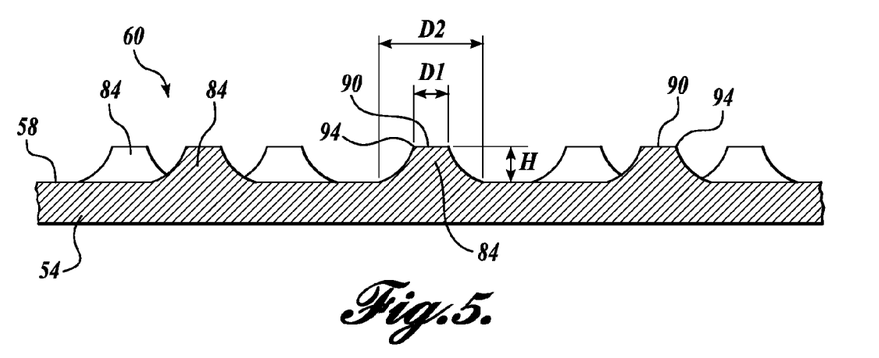
FIG. 5 is a partial side view of one example of a surface having abrasive elements thereon in accordance with aspects of the present disclosure.

Referring now to FIGS. 3 and 5-7, aspects of the surface 58 having abrasive sections 60 thereon will now be described in more detail. As shown in FIG. 5, the abrasive sections 60 of the outwardly facing surface 58 include a plurality of spaced apart, abrasive elements 84 sufficiently configured to exfoliate dead skin of a subject's epidermis. In that regard, the abrasive elements 84 may be also be referred to herein as exfoliating projections 84. As will be explained in more detail below, the abrasive elements 84 can have many configurations, depending in part on its intended application.

In some embodiments, the plurality of abrasive elements 84 are configured to provide generalized dead skin removal in areas of the body, such as the hand, elbow, or foot. In other embodiments, the plurality of abrasive elements are configured to provide for more aggressive engagement with the skin in order to sculpt and/or smooth rough areas of the body, such as the hands or feet, where calluses, corns, etc., have developed. In embodiments of the present disclosure, the abrasive elements 84 do not include bristles. As such, exfoliating heads in these embodiments can be referred to as brush-less exfoliating heads.

Each of the abrasive elements 84 can have the same or similar configuration across the surface 58. Alternatively, the configurations of the abrasive elements 84 may vary throughout the surface 58 or between abrasive sections 60. As will be described in more detail below, the abrasive elements 84 in some embodiments project outwardly from the surface 58 of the disc plate 56 to a height in a range of about 0.003 inches (0.0762 millimeters) to about 0.008 inches (0.203 millimeters). In some embodiments, the disc plate includes up to 2200 abrasive elements per square inch over sections of the surface 58.

It will be appreciated that in some embodiments, the abrasive elements 84 can be arranged in random fashion while in other embodiments the abrasive elements 84 can be arranged in one or more patterns. In these embodiments, the one or more patterns can be constant throughout the majority of the surface 58 or can vary throughout the majority of the surface 58 or parts thereof. In the embodiment shown, the surface includes a section 86 located at the center thereof that is absent of any abrasive elements 84. In some embodiments, the section 86 has a smooth surface in order to aid in the prevention of premature stalling of the central portion 44 when traversing over curved surfaces of a subject and the like. In these embodiments, the smooth surface of section 86 occupies about 10% or more of the surface 58.

In accordance with some aspects of the present disclosure, the abrasive elements 84 can be embedded, adhered, attached, formed, disposed or otherwise provided on the outwardly facing surface 58 via an additive process. In some embodiments, the abrasive elements 84 are comprised of small abrasive particles including, but not limited to diamond chips or diamond dust, silicon carbide, aluminum oxide, sand, such as silica, calcium carbonate, etc., alumina-zirconium, pumice, and combinations thereof. In some embodiments, the average diameter of the abrasive particles is in the range of about 45 microns to about 250 microns, or greater.

In one of the more simple examples of an additive process that can be employed to form the abrasive elements 84, sandpaper or the like, having grit of between 60-300, can be adhesive bonded to the surface 58 of the disk plate 54. Another additive process that may be employed in some embodiments is plating or coating. For example, in embodiments where the disc plate 54 is made of metal, a layer of metal such as nickel, silver, gold, titanium, zirconium, chromium, and/or their oxides, dioxides, etc., having a slurry of abrasive particles disposed therein can be plated to the disc plate 54 using electro or electro-less plating methods, vacuum deposition techniques, such as chemical vapor deposition, physical vapor deposition, etc., sputtering deposition, cathodic arc deposition, plasma deposition, among others.

In embodiments where the disc is made of plastic, the abrasive elements 84 can be secured thereto, for example, by first creating a thin base layer of, for example, silver or gold, using vacuum deposition techniques. Once the base layer is applied to the disc plate 54, a layer of metal such as nickel, silver, gold, titanium, zirconium, chromium, and/or their oxides, dioxides, etc., having a slurry of abrasive particles disposed therein can be plated to the base layer using an electro or electro-less plating method. In addition to electro or electro-less plating, other techniques could be used to secure the abrasive particles to a plastic disc plate, such as by using adhesive bonding, plasma deposition, among others. In other embodiments, the disc plate 54 can be co-molded with a plastic resin having abrasive particles disposed therewith.

In accordance with other aspects of the present disclosure, the abrasive elements 84 can be also formed or otherwise provided on the outwardly facing surface 58 via a subtractive process. In some embodiments, a pulsed laser deposition process may be employed. In other embodiments, the abrasive elements 84 are chemically etched into the surface 58 of the disc plate 54. In this regard, in some embodiments, the disc plate 54 is photo-etched according to a predetermined pattern and etching protocol to form the exfoliating projections on the surface of the disc plate 54.

FIG. 5 is a partial, magnified view of the geometry of one example of the abrasive elements 84 formed by an etching process in accordance with aspects of the present disclosure. As best shown in the side view of FIG. 5, the abrasive elements 84 are generally frusto-conical in shape, having a generally flat top surface 90 that generally define cutting edges 94. The diameter D1 of the top surface 90 is about 30%-60% of the diameter D2 of the base of the abrasive element 84 in some embodiments, and about 48-52% in other embodiments. In various embodiments, the diameter D1 of the top surface 90 is in the range of 0.004 inches (0.0102 millimeters) to 0.008 inches (0.203 millimeters). While shown and described as being generally-frusto-conical, the abrasive elements may have other inwardly tapered and truncated geometries, such as a truncated pyramid (e.g., frusto-pyramidal, etc.).

Figure 6:
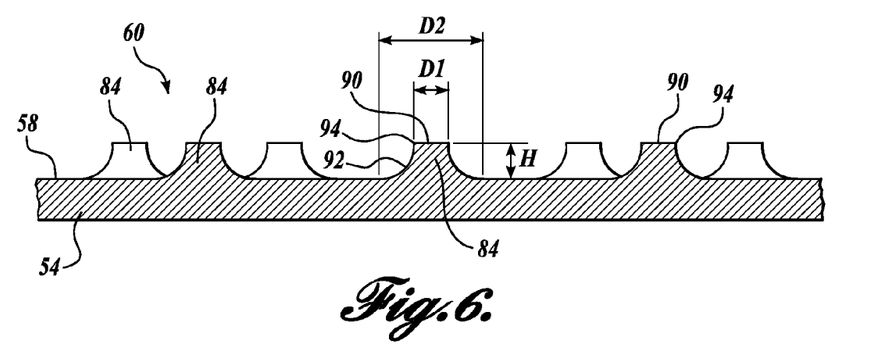
FIG. 6 is a partial side view of another example of a surface having abrasive elements thereon in accordance with aspects of the present disclosure.
Figure 7:
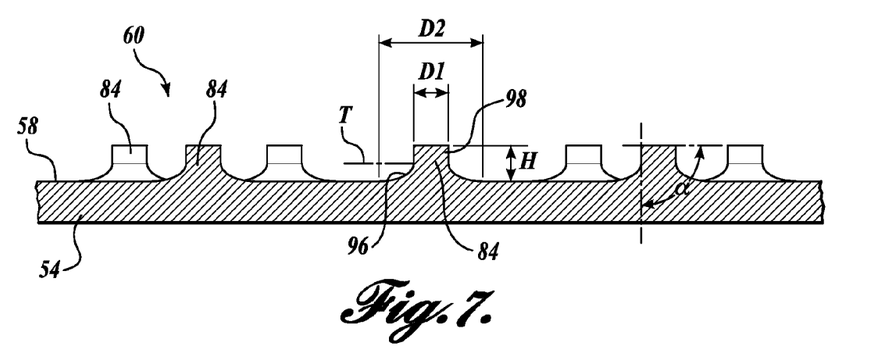
FIG. 7 is a partial side view of another example of a surface having abrasive elements thereon in accordance with aspects of the present disclosure.

Other characteristics of the abrasive elements 84 include projection heights H of approximately 0.004 inches (0.0102 millimeters) to 0.008 inches (0.203 millimeters) in some embodiments, and heights H of about 0.006 inches (0.152 millimeters) and 0.008 inches (0.203 millimeters) in other embodiments. In some embodiments, the disc plate 54 can be somewhat over-etched, thereby creating generally concave side walls 92 or portions thereof, as best shown in the example of FIG. 6. In other embodiments, a more pronounced top or cutting edge 94 of the top surface 90 can be formed, as best shown in FIG. 7. In this embodiment, the side walls of the abrasive elements 84 include a generally frusto-conical base section 96 and a generally cylindrical top section 98. In some embodiments, the side walls transition (designated "T") from the base section 96 to the top section 98 from about 0.0005 inches (0.0127 millimeters) to 0.002 inches (0.0508 millimeters) from the top surface 90. In some embodiments, the angle α created between the side walls of the top section 98 and the top surface 90 is preferably no more than 90 degrees.

The aforementioned geometry of one or more embodiments of the abrasive elements can be formed by an etching process. However, it will be appreciated that abrasive elements having one or more of these characteristics can be achieved with other methods of manufacture, including both additive and subtractive processes described herein. Moreover, a thin film (e.g., 0.0001 inches (0.00254 millimeters)) of titanium dioxides, zirconium dioxides, chromium dioxides, gold, silver, copper, zinc, etc., can be coated onto the abrasive elements 80 via conventional coating techniques in order to improve lubricity and/or biocompatibility of the abrasive surface, if desired.

The above-described examples of the exfoliating head 20 can be used to exfoliate skin of a subject's epidermis, and in some embodiments, reduce or remove rough skin conditions caused by partially keratinized cells, such as calluses or corns. In that regard, the exfoliating head 20 is first attached to the personal care appliance 22. Next, the personal care appliance 22 is turned on and the exfoliating head 20 is operated at frequencies in the range of 90-300 Hz, oscillating the exfoliating head 20 back and forth within a range of 8-26 degrees. In some embodiments, the exfoliating head 20 is operated at frequencies of about 100 Hz to 190 Hz with an amplitude or range of about 12-18 degrees. In other embodiments, the exfoliating head 20 is operated at frequencies of about 168 Hz to 178 Hz, an amplitude or range of about 12-18 degrees and a duty cycle of between about 36%-48%.

Once oscillating, the abrasive surface of the exfoliating head 20 is applied against and traversed over the rough areas of skin on the body, such as on the feet or hands. The oscillatory action of the abrasive surface, operated at the above amplitudes and frequencies, provides an exfoliating effect, thereby sculpting the rough areas of skin and the removal or reduction of corns, calluses, etc. In some embodiments, the system is configured such that if the user applies too much force against the skin, the system will stall. Once the areas are sculpted to the desired amount, the abrasive surface of the exfoliating head 20 can be removed from the skin and the appliance 22 can be powered down. Alternatively, the appliance 22 can be powered down automatically via a programmed operation.

Thus, using examples of the exfoliating head 20 as described above, in the specified frequency and amplitude ranges, in the representative process outlined above, results in improved control and precision for skin sculpting and/or callus/corn removal. Additional benefits may also be realized when exfoliating skin with the exfoliating head 20. For example, since skin can be removed with each directional change of the head 20 as a result of the oscillating motion imparted thereon, more skin can be removed with less force as compared to conventional rotary powered devices or manually powered devices.

The method described above can be carried-out without an attempt to soften the skin by the use of skin care formulas or soaking of the skin in warm water. However, any preparation of the skin area prior to exfoliation can be used as part of the method disclosed above.

It should be noted that for purposes of this disclosure, terminology such as "upper," "lower," "vertical," "horizontal," "fore," "aft," "inner," "outer," "inwardly," "outwardly," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The embodiments of the invention in which an exclusive property or privilege is claimed are defined as follows:

1. A brush-less exfoliating head for use with a personal care appliance having a drive system, comprising:
    a movable base portion configured to be operatively coupled to the drive system;
    a disc plate mounted on the movable base portion; and
    a plurality of abrasive elements provided on a surface of the disc plate and positioned to project outwardly from the surface to a height of about 0.003 inches to about 0.008 inches, the abrasive elements configured to exfoliate a partially keratinized area of an epidermis when placed in contact therewith,
    wherein the disc plate includes a continuous section covering at least 10% of the surface and located near a center of the disc plate, the continuous section having a smooth surface that is absent of the plurality of abrasive elements;
    wherein the plurality of abrasive elements are located outwardly from a perimeter of the continuous section and positioned at a plurality of radial distances from the center of the disc plate,
    wherein each abrasive element forms a frustum comprising:
        a base positioned adjacent the disc plate;
        a top surface spaced outwardly a distance from the base; and
        one or more side walls that extend from the base and adjoin with the top surface to form one or more cutting edges, and wherein each abrasive element narrows as each abrasive element extends from the base of the abrasive element towards the top surface of the abrasive element,
    wherein a ratio, as a percentage, of a cross-sectional area of the top surface of each abrasive element to a cross-sectional area of the base of each abrasive element is between 30% and 60%.

2. The brush-less exfoliating head of claim 1, wherein the top surface of each abrasive element has a diameter of 0.004 inches to 0.008 inches.

3. The brush-less exfoliating head of claim 2, wherein the top surface of each abrasive element is generally flat and lies within a plane that is generally parallel with the surface of the disc plate.

4. The brush-less exfoliating head of claim 1, wherein the ratio is between 48%-52%.

5. The brush-less exfoliating head of claim 1, wherein the one or more side walls includes a top section adjoining the top surface, wherein the top section is configured to adjoin the top surface at the cutting edges and form an angle therebetween, wherein the angle is less than or equal to 90 degrees.

6. The brush-less exfoliating head of claim 5, wherein the top section for each abrasive element begins about 0.0005 to 0.002 inches from the top surface.

7. The brush-less exfoliating head of claim 1, wherein the continuous section is circular and located at the center of the disc plate.

8. The brush-less exfoliating head of claim 1, wherein the plurality of abrasive elements are rigid.

9. The brush-less exfoliating head of claim 8, wherein the disc plate includes metal.

10. The brush-less exfoliating head of claim 1, wherein the plurality of abrasive elements are selected from a group consisting of diamond chips, diamond dust, silicon carbide, aluminum oxide, silica, calcium carbonate, alumina-zirconium, pumice, and etched projections.

11. The brush-less exfoliating head of claim 1, wherein the one or more side walls of each abrasive element includes a concave section.

12. An exfoliating workpiece, comprising:
    a disc plate; and
    a plurality of etched abrasive elements disposed on a surface of the disc plate and positioned to project outwardly from the surface about 0.003 inches to 0.008 inches, each abrasive element forming a frustum comprising:
        a base positioned adjacent the disc plate;
        a top surface spaced outwardly a distance from the base; and
        at least one side wall that extends from the base and adjoins with the top surface to form one or more cutting edges, wherein the at least one side wall includes a surface having a concave curvature that adjoins the one or more cutting edges,
    wherein the disc plate includes a continuous section covering at least 10% of the surface and is absent of the plurality of abrasive elements, the continuous section covering at least a center of the disc plate, wherein the plurality of abrasive elements are located outwardly from a perimeter of the continuous section and positioned at a plurality of radial distances from the center of the disc plate;
    wherein a ratio, as a percentage, of a cross-sectional area of the top surface of each abrasive element to a cross-sectional area of the base of each abrasive element is between 30% and 60%.

13. The exfoliating workpiece of claim 12, wherein the top surface has a diameter between the range of 0.004 inches and 0.008 inches.

14. The exfoliating workpiece of claim 12, wherein at least one section of the disc plate includes about 2200 abrasive elements per square inch.

15. A system, comprising:
a personal care appliance having an oscillating drive system; and
a brush-less exfoliating workpiece configured to be operatively coupled to the oscillating drive system, wherein the workpiece comprises:
a disc plate; and
a plurality of abrasive elements provided on a surface of the disc plate and positioned to project outwardly from the surface, the abrasive elements configured to exfoliate a partially keratinized area of an epidermis when oscillated in contact therewith,
wherein each abrasive element forms a frustum comprising:
a base positioned adjacent the disc plate;
a top surface spaced outwardly a distance from the base; and
a plurality of side walls that extend from the base and adjoin with the top surface to form one or more cutting edges, and wherein each abrasive element narrows as each abrasive element extends from the base of the abrasive element and widens at the top surface of the abrasive element, the base being wider than the top surface; and
wherein the disc plate includes a continuous section that is absent of the plurality of abrasive elements, the continuous section covering at least a center of the disc plate and at least 10% of a surface of the disc plate from which the plurality of abrasive elements project outwardly, and wherein the plurality of abrasive elements are located outwardly from a perimeter of the continuous section and positioned at a plurality of radial distances from the center of the disc plate.

16. The system of claim 15, wherein at least one of the plurality of side walls of each abrasive element includes a concave section.

17. The system of claim 15, wherein the plurality of abrasive elements include etched abrasive elements.

18. The system of claim 15, wherein the plurality of abrasive elements project outwardly from the disc plate from 0.003 inches to 0.008 inches, and wherein each top surface has a diameter of 0.004 inches to 0.008 inches.

19. The system of claim 18, wherein a ratio, as a percentage, of a cross-sectional area of the top surface of each abrasive element to a cross-sectional area of the base of each abrasive element is between 30% and 60%.

20. The system of claim 19, wherein the ratio is between 48%-52%.

* * * * *